United States Patent [19]
Belanger et al.

[11] Patent Number: 5,929,336
[45] Date of Patent: *Jul. 27, 1999

[54] DRY BEARING DETECTION APPARATUS

[75] Inventors: David J. Belanger, Waukesha, Wis.;
Palmer H. Beam, Westminster, Colo.;
George J. Eilers, Evergreen, Colo.;
Daniel R. Mohrbacher; Douglas P. Miller, both of Lakewood, Colo.

[73] Assignee: Sundstrand Fuild Handling Corporation, Arvada, Colo.

[*] Notice: This patent issued on a continued prosecution application filed under 37 CFR 1.53(d), and is subject to the twenty year patent term provisions of 35 U.S.C. 154(a)(2).

[21] Appl. No.: 08/760,948

[22] Filed: Dec. 9, 1996

[51] Int. Cl.$^6$ .................................................. G01N 29/10
[52] U.S. Cl. .............................................. 73/593; 73/660
[58] Field of Search ............................ 73/10, 593, 660, 73/598, 600, 596, 609–616

[56] References Cited

U.S. PATENT DOCUMENTS

| | | | |
|---|---|---|---|
| 4,018,082 | 4/1977 | Manoliu et al. | 73/618 |
| 4,376,389 | 3/1983 | Inoue et al. | 73/118 |
| 4,387,596 | 6/1983 | Fenkner et al. | 73/593 |
| 4,493,042 | 1/1985 | Shima et al. | 364/507 |
| 4,584,865 | 4/1986 | Hutchins | 73/7 |
| 4,748,850 | 6/1988 | Kataoka | 73/660 |
| 4,924,180 | 5/1990 | Nasr et al. | 324/207.15 |
| 4,995,259 | 2/1991 | Khuri-Yakub et al. | 73/593 |
| 5,072,611 | 12/1991 | Budd et al. | 73/10 |
| 5,140,849 | 8/1992 | Fujita et al. | 73/593 |
| 5,140,858 | 8/1992 | Nishimoto et al. | 73/587 |
| 5,277,543 | 1/1994 | Noguchi et al. | 415/118 |
| 5,336,996 | 8/1994 | Rusnak | 324/207.2 |
| 5,350,040 | 9/1994 | Gribble | 73/593 |
| 5,696,444 | 12/1997 | Kipp et al. | 324/207.32 |

FOREIGN PATENT DOCUMENTS

| | | | |
|---|---|---|---|
| 0 759 544 A1 | 2/1997 | European Pat. Off. | G01K 1/02 |
| 0 759 545 A1 | 2/1997 | European Pat. Off. | G01K 1/02 |
| 173151 | 8/1986 | Japan . | |
| 89/12528 | 12/1989 | WIPO . | |

OTHER PUBLICATIONS

Product Brochure entitled: "Protect your Pumps from Dry Running" created in Jul. 1996 for Ansimag Inc. of Elk Grove Village, Illinois.
Dry–Kut Instruction Manual for "Monitors to Protect Your Pumps from Dry–Running and Overloading" created in 1996 for Ansimag, Inc. Of Elk Grove Village, Illinois.
Sundstrand Fluid Handling Brochure entitled "Sundyne Vertical Integrated Pump", Bulletin 11.1, dated Feb., 1992.
Sundstrand Fluid Handling Brochure entitled "Sundyne Canned Motor Pumps", Bulletin 1.4, dated Aug., 1995.

*Primary Examiner*—Hezron Williams
*Assistant Examiner*—Rose M. Miller
*Attorney, Agent, or Firm*—Marshall, O'Toole, Gerstein, Murray & Borun

[57] ABSTRACT

Apparatus for detecting a dry bearing condition utilizes an ultrasonic transducer which is intermittently pulsed a certain number of times by a microprocessor and associated circuitry. The number of return pulses received by the ultrasonic transducer is detected by the microprocessor and is used to determine whether a dry bearing condition exists.

18 Claims, 7 Drawing Sheets

5,929,336

DRY BEARING DETECTION APPARATUS

TECHNICAL FIELD

The present invention relates generally to detectors, and more particularly to apparatus for detecting when a machine bearing is dry.

BACKGROUND ART

Machines that have relatively movable parts include bearings. In those situations where there is direct contact between relatively moving parts, consideration must be given to the problem of wear. Typically, bearing materials are selected and/or a lubricant is used so that adequate service life is obtained and so that the risk of catastrophic failure is minimized. In some machines, lubrication is provided by process fluid. One example of such a machine is a sealless pump (also referred to as a canned motor pump or magnetic drive pump) which is used to pump fluids that must be isolated from the ambient environment. In one type of sealless pump, a motor stage and a pump stage are disposed within a single housing and include a common rotor coupled to a pump impeller. The rotor is supported by radial journal and axial thrust bearings lubricated with process fluid. These bearings are made of a relatively soft carbon or wear resistant ceramic material. Typically, lubrication by the process fluid is marginal, and intermittent dry operation is encountered. While short periods of operation without substantial lubrication can be tolerated, longer periods of dry bearing operation can result in a costly and potentially hazardous situation.

Conventionally, a wattmeter is used to measure the power expended by the motor. If process fluid is absent in the pump stage, then the power consumed by the motor drops, and this condition is sensed by the wattmeter to detect the probability of a dry bearing condition. However, a situation can arise wherein process fluid is present at the pump impeller but is not present at one of the bearings. In this case, the wattmeter would fail to indicate the dry bearing condition.

SUMMARY OF THE INVENTION

An apparatus for detecting a dry bearing condition directly detects the presence of fluid in a bearing so that detection reliability is improved.

More particularly, according to one aspect of the present invention, an apparatus for detecting when a bearing disposed in a bearing housing is operating under a dry bearing condition includes an ultrasonic sensor directed toward the bearing housing, an excitation circuit which provides excitation to the ultrasonic sensor to cause ultrasonic energy to be directed toward the bearing housing and a detection circuit which detects reflected ultrasonic energy from the bearing housing.

Preferably, the excitation circuit includes a microprocessor which causes the ultrasonic sensor to direct a pulse of ultrasonic energy toward the bearing housing. Also preferably, the excitation circuit further includes a one-shot coupled to the microprocessor and a driver circuit coupled to the one-shot.

The detection circuit may comprise either the same or a different microprocessor as that noted above and which determines that a return pulse of ultrasonic energy has been received by the ultrasonic sensor. Still further, the microprocessor may include a timer which establishes a time period during which a return pulse is expected to be received by the ultrasonic sensor. The detection circuit preferably further comprises a comparator coupled to the ultrasonic sensor and a one-shot coupled between the comparator and the microprocessor.

Still further in accordance with the preferred embodiment, the ultrasonic sensor is operated to direct a number of pulses of ultrasonic energy toward the bearing housing and the microprocessor includes means for determining whether a certain number of return pulses of ultrasonic energy has been received by the ultrasonic sensor.

In accordance with alternative embodiments, the ultrasonic sensor is radially or axially spaced from the bearing.

According to an alternative aspect of the present invention, an apparatus for detecting when a rotary bearing is operating under a dry bearing condition includes a piezoelectric transducer disposed proximate the bearing and having a transducer face directed toward the vicinity of the bearing and an excitation circuit for providing excitation to the piezoelectric transducer to cause ultrasonic energy to be directed toward the bearing vicinity. A detection circuit is also provided for detecting whether the ultrasonic energy is reflected from the bearing vicinity.

According to yet another aspect of the present invention, an apparatus for detecting when a rotary bearing is operating under a dry bearing condition includes means disposed proximate the bearing for converting between electrical energy and acoustic energy, means for exciting the converting means to cause a pulse of ultrasonic energy to be directed toward the bearing and means coupled to the converting means for detecting whether the pulse of ultrasonic energy is reflected from the bearing.

Other features and advantages will become apparent from the specification and drawings of the present application, in which like reference numerals denote like structures.

DESCRIPTION OF THE PREFERRED EMBODIMENTS

Figure 1:
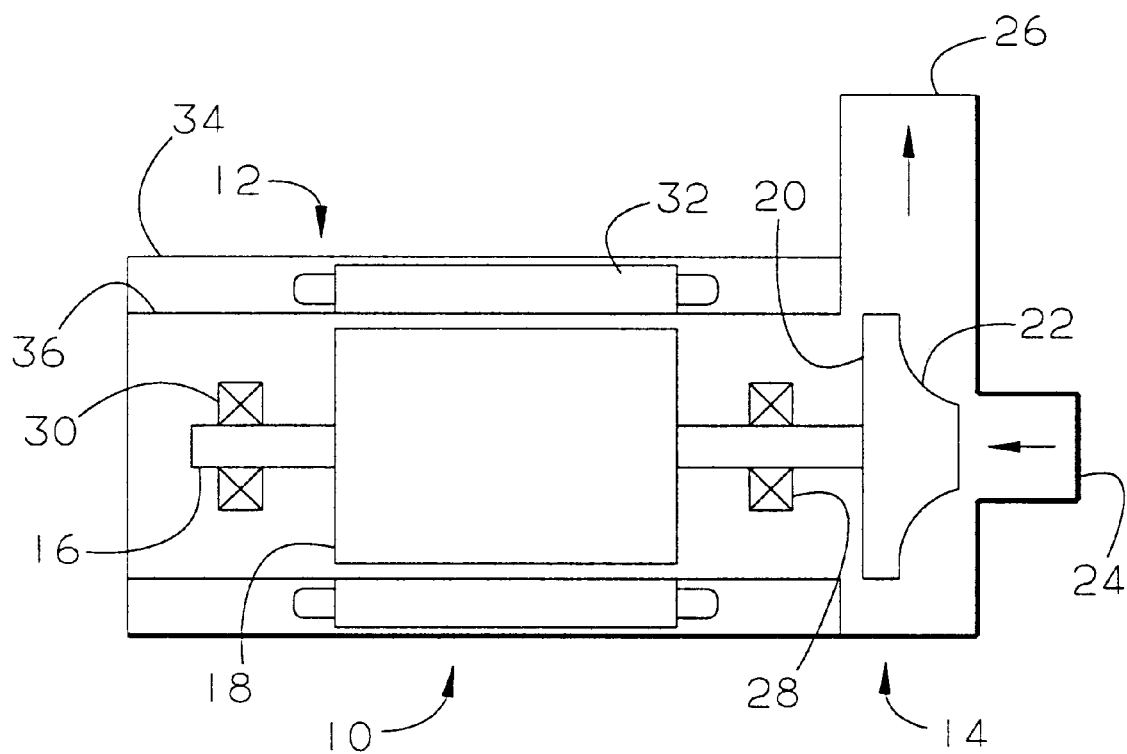
FIG. 1 comprises a diagrammatic view of a sealless pump incorporating the present invention.

Referring now to FIG. 1, a sealless pump 10 includes a motor stage 12, a pump stage 14 and a rotor structure 16. In the illustrated pump 10, the rotor structure 16 is common to the stages 12 and 14 and includes a motor stage portion 18 and a pump stage portion 20 wherein the latter includes an impeller 22 which pressurizes a process fluid entering the pump 10 at a pump inlet 24. The pressurized process fluid is discharged through a pump outlet 26. The rotor structure 16 is mounted for rotary motion in front and rear bearings 28, 30, respectively. Process fluid is introduced to the vicinity of the bearings 28, 30 to lubricate same. A stator structure 32 of the motor stage 12 is encased between an outer housing 34 and an inner sleeve 36 to isolate the stator structure from the process fluid.

It should be noted that the pump 10 need not have the configuration shown in FIG. 1. For example, the pump 10 may have completely separate motor and pump stages interconnected by a shaft. In fact, the present invention could be used in a completely different machine inasmuch as it finds utility in any environment where a mechanical bearing must be lubricated and/or where the presence (or absence) of liquid must be detected.

Figure 2:
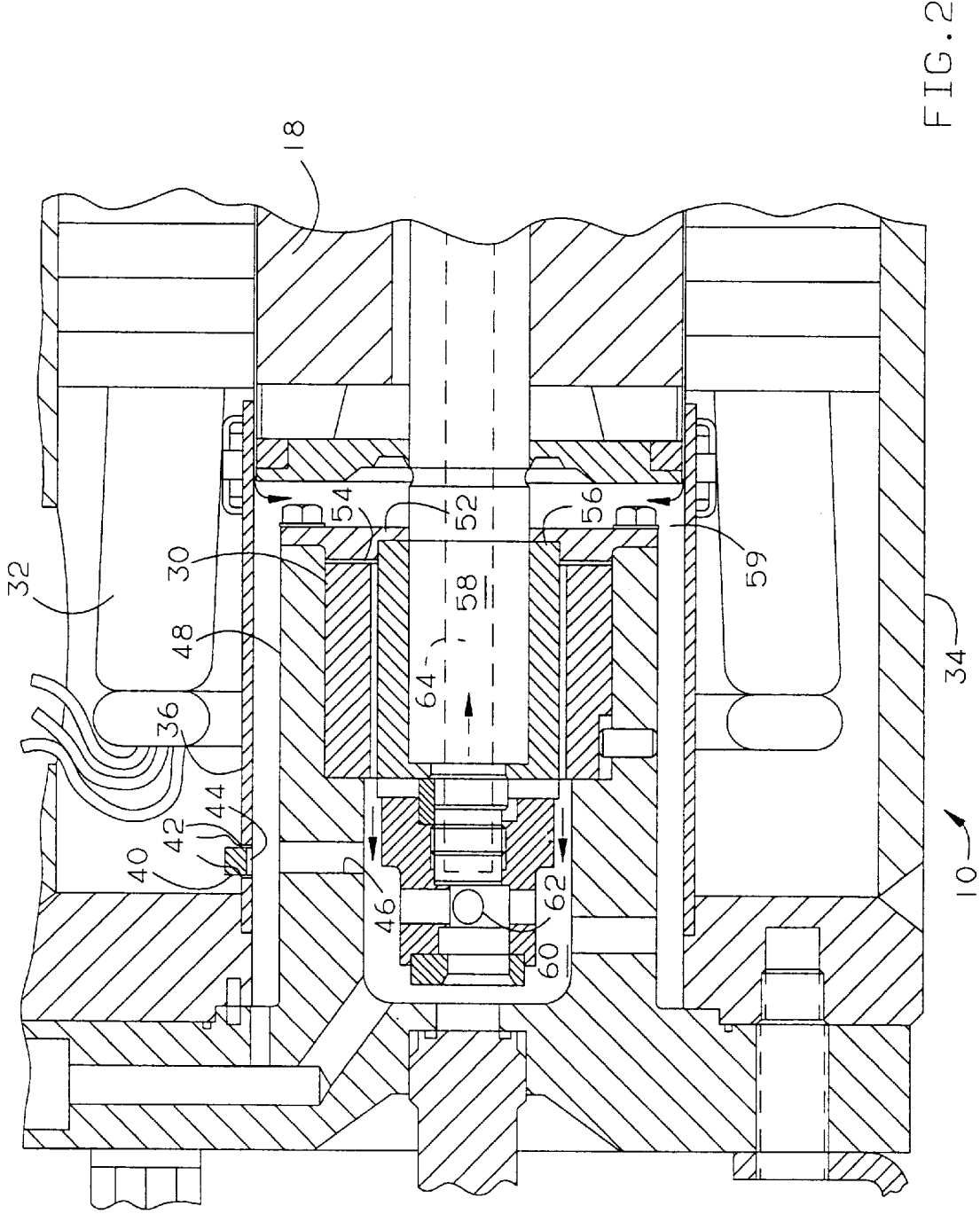
FIG. 2 comprises an enlarged, fragmentary sectional view of a portion of the sealless pump of FIG. 1 illustrating a first embodiment of the present invention.

FIG. 2 illustrates a first embodiment wherein an ultrasonic transducer in the form of a piezoelectric element 40 is disposed radially outside the rear bearing 30. In this embodiment, the element 40 is secured to a pad 42 which, in turn, is mounted within a recess 44 formed in the inner sleeve 36. The pad 42 has a planar upper surface to which the element 40 is secured by adhesive or any other suitable means and a curved lower surface shaped to fit against the bottom surface of recess 44. The pad 42 is mounted in any convenient fashion, such as by welds, to the inner sleeve 36. The mounting of the element 40 and the pad 42 to the sleeve 36 should be effected in a manner which insures that ultrasonic energy is transmitted at an appreciable magnitude through the sleeve 36 toward the vicinity of the bearing 30.

Further, it should be noted that the element 40 may be curved to fit the shape of the sleeve 36, in which case the element can be secured directly thereto, thereby obviating the need for the pad 42.

A hole 46 extends through a bearing housing 48 and channels ultrasonic energy toward the vicinity of the rear bearing 30. The bearing 30 is secured to the bearing housing 48 by an end plate 52 bolted to an end surface 54 of the bearing housing 48. An inner bearing sleeve 56 is secured in any suitable fashion to a rotor shaft 58. During normal operation of the pump 10, process fluid flows in the annular space between the rotor structure and the inner sleeve 36 and enters an outer chamber 59. The fluid then passes through the annular gap between the bearing 30 and the inner bearing sleeve 56 and enters an end chamber 60 (the annular gap between the bearing 30 and the sleeve 56 is exaggerated in the Figs. for the sake of clarity). The process fluid then enters a port 62 and returns to the pump stage portion 20 through a bore 64 in the rotor shaft 58.

Figure 3:
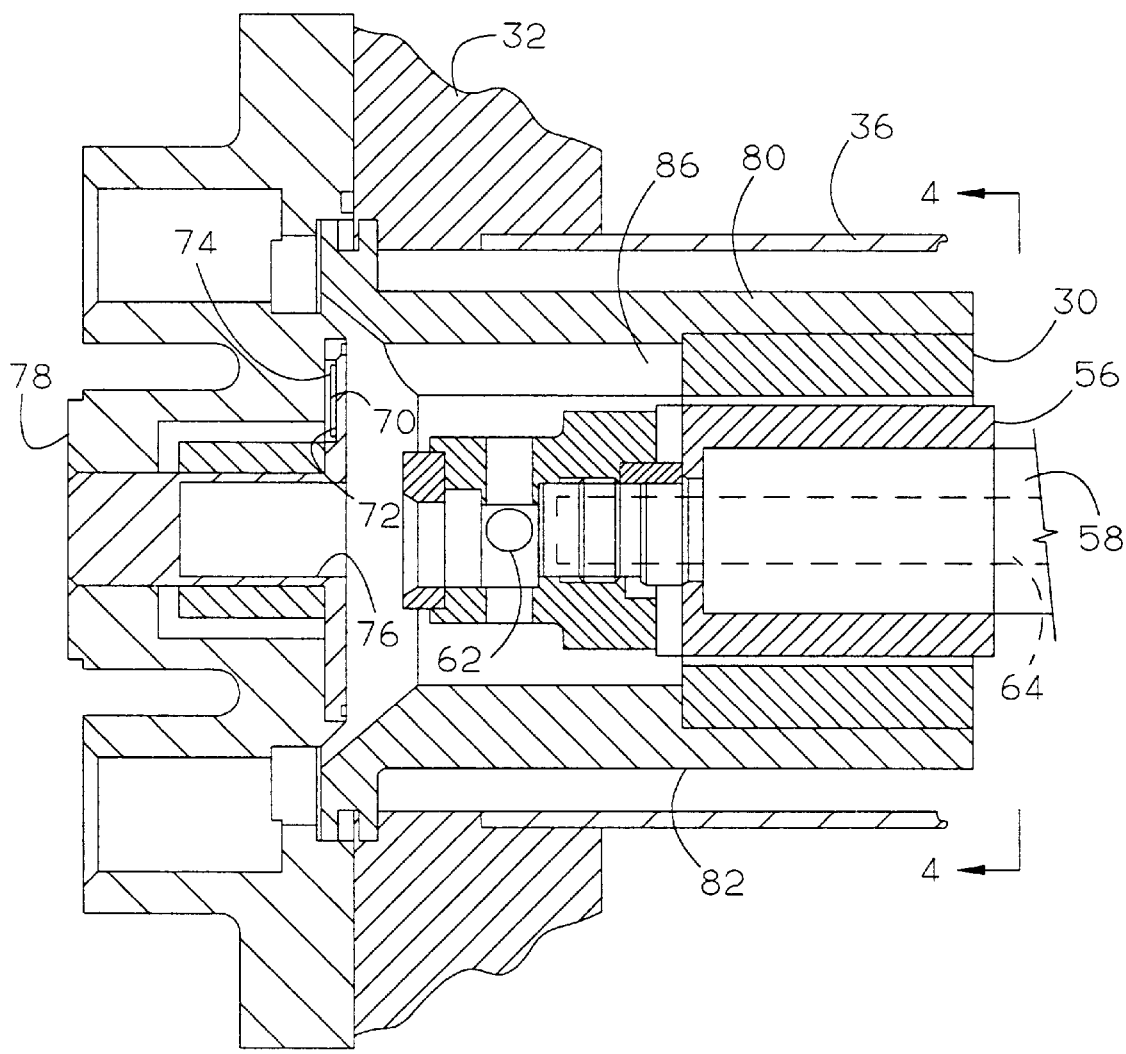
FIG. 3 comprises a view similar to FIG. 2 illustrating a second embodiment of the present invention.
Figure 4:
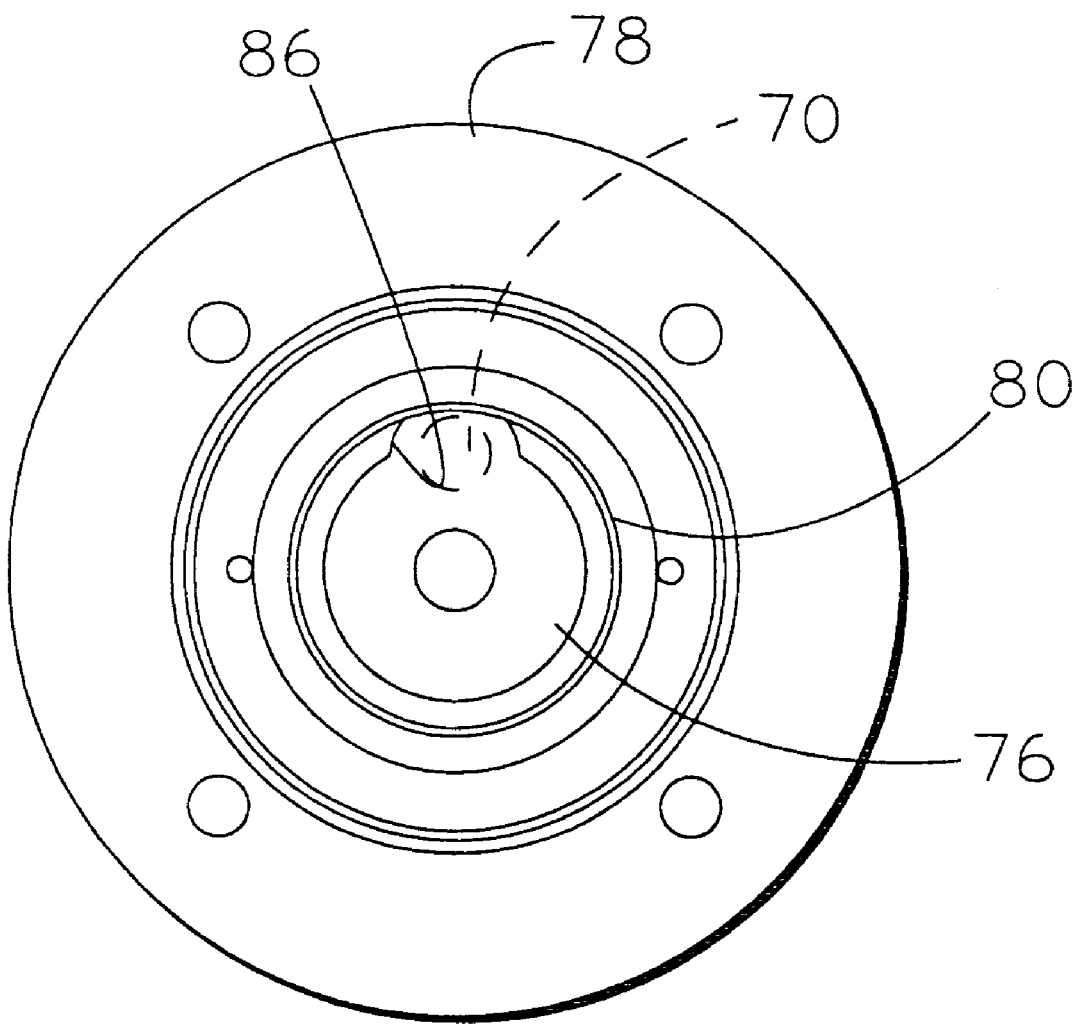
FIG. 4. comprises an end elevational view of the sensor housing of FIG. 3 taken generally along the lines 4—4 of FIG. 3.

The embodiment of FIGS. 3 and 4 differs from that of FIG. 2 in that an ultrasonic transducer in the form of a piezoelectric element 70 is axially spaced from the rear bearing 30. The element 70 is mounted by adhesive or any other suitable means on a base surface 72 of a recess 74 formed in a central sleeve 76. The central sleeve 76 is secured by any suitable means in an outer plate member 78. The outer plate member 78, in turn, is secured by any suitable means (such as bolts) to the stator structure 32, thereby clamping an annular flange of a cylindrical inner member 80 in stationary position against the stator structure 32. The central sleeve 76 and the members 78, 80 are therefore rigidly secured to the stator structure 32 and together form a bearing housing 82 to which the rear bearing 30 is secured in any suitable fashion. As seen in FIG. 4, the cylindrical inner member 80 includes walls defining an enlarged recess 86 which permits ultrasonic energy developed by the element 70 and transmitted through the central sleeve 76 to reach the bearing 30.

The embodiment of FIGS. 3 and 4 is preferred over that of FIG. 2 because the element 70 is mounted on a flat surface, and hence, a pad or other intervening member is not required.

Figure 5:
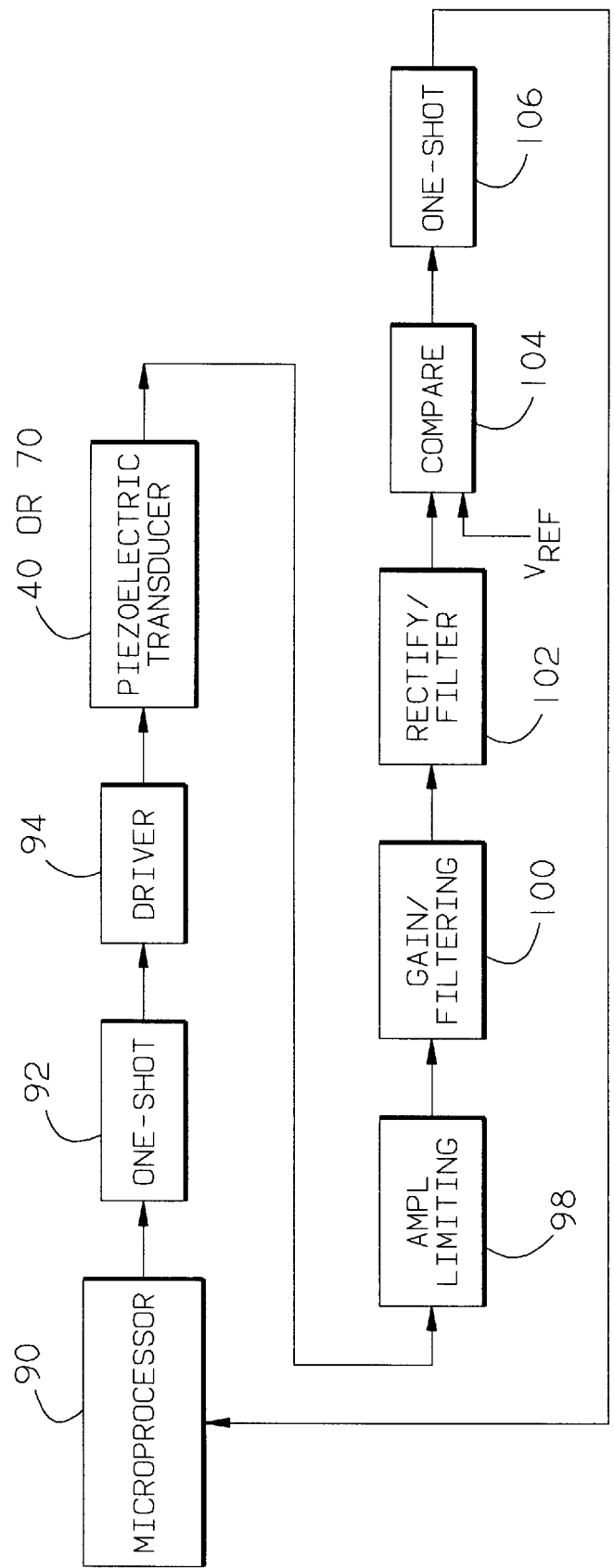
FIG. 5 comprises a block diagram of circuitry coupled to the piezoelectric transducer of FIG. 3.

FIG. 5 illustrates a block diagram of circuitry usable with either of the foregoing embodiments. A microprocessor 90 develops control pulses which are applied to a one-shot or pulse generator 92. The latter circuit develops pulses of appropriate duration which are applied to a driver circuit 94, which, in turn, provides trigger pulses of appropriate magnitude and waveshape to the piezoelectric element 40 or 70. In response thereto, the element 40 or 70 directs ultrasonic pulses toward the bearing housing 48 or 82, respectively. Ultrasonic energy resulting from initial excitation of the element 40 or 70 as well as reflected ultrasonic energy is converted back into an electric signal (the latter is also referred to as a return signal) by the element 40 or 70. An amplitude limiting circuit 98 is provided to limit the amplitude of the signal caused by the initial excitation of the element 40 or 70. A gain/filter circuit 100 and rectifier/filter circuit 102 condition the return signal and the resulting signal is compared to a reference voltage $V_{REF}$ by a comparator 104. A pulse generator or one-shot 106 develops a pulse of certain duration each time the conditioned return signal exceeds the reference voltage $V_{REF}$. The output of the one-shot 106 is detected by the microprocessor 90.

Figure 6A:
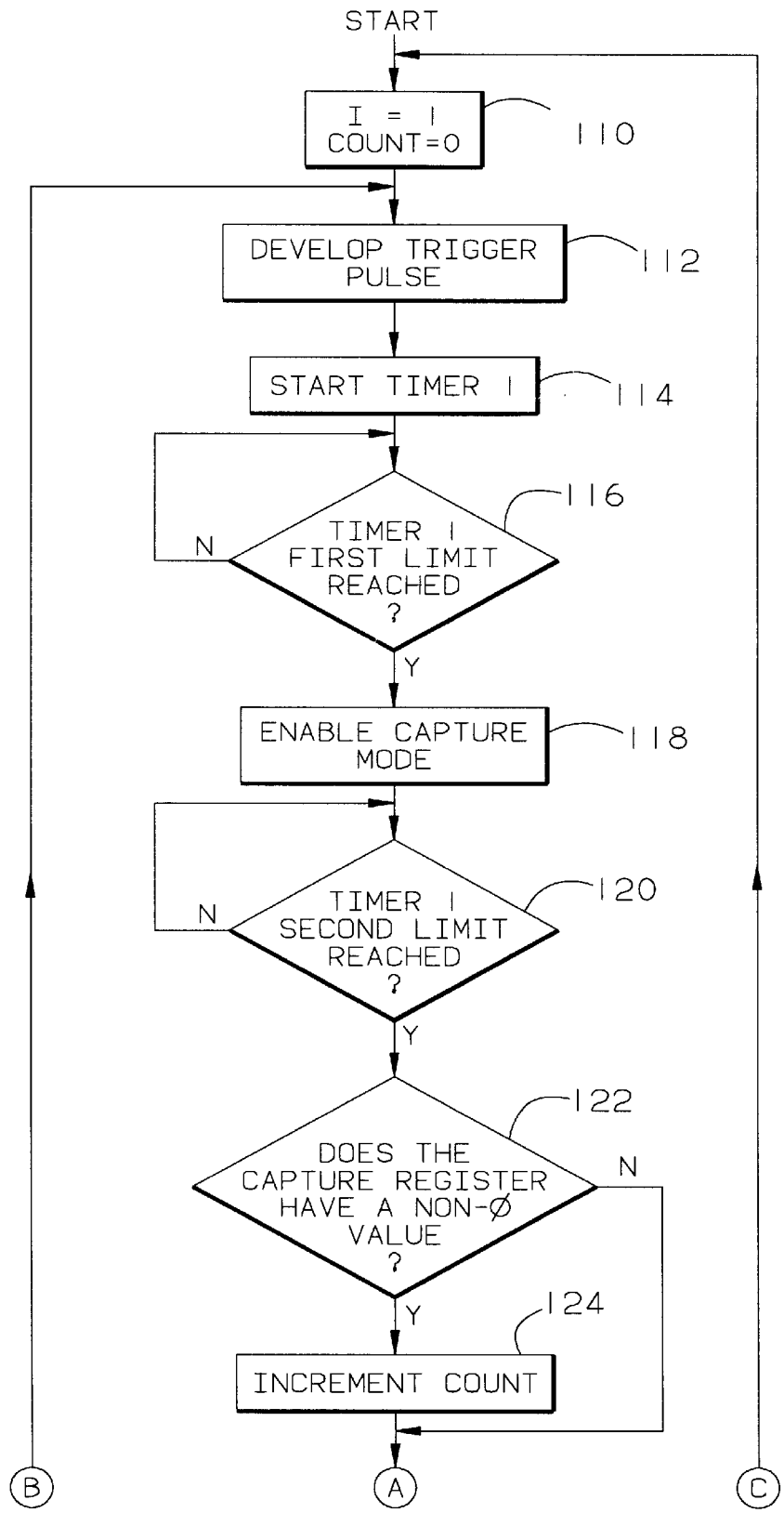
FIGS. 6a and 6b, when joined along the similarly lettered lines, together comprise a flowchart executed by the processor of FIG. 5 to implement the preferred embodiment of the present invention.
Figure 6B:
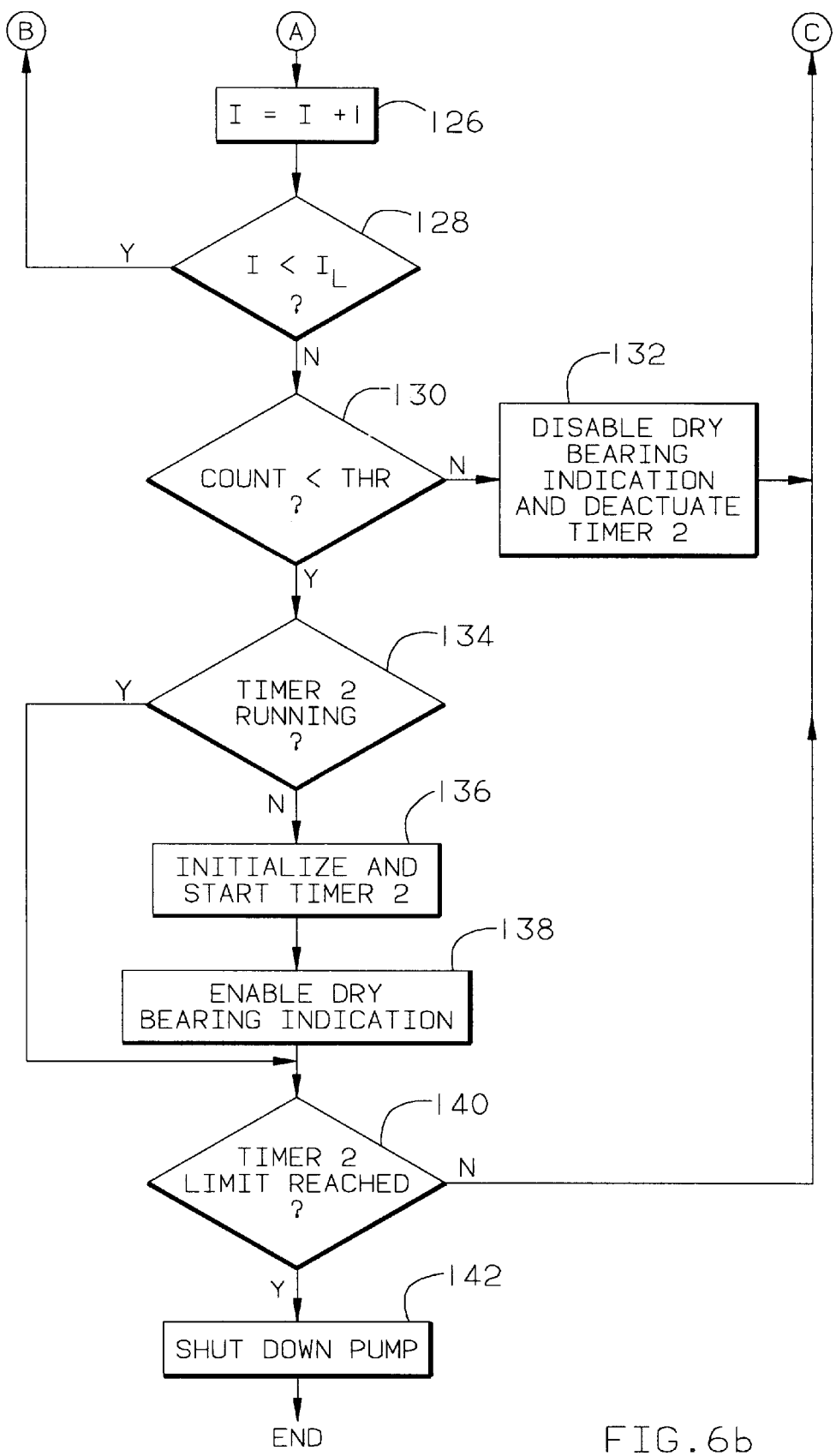

FIGS. 6a and 6b illustrate programming executed by the microprocessor 90 of FIG. 5 to implement the present invention. The programming begins at a block 110, where a loop counter I is set equal to one and a microprocessor counter COUNT is set equal to zero. A block 112 then develops a trigger pulse which is sent to the circuits 92 and 94 of FIG. 5 and thence to the element 40 or 70 so that a pulse of ultrasonic energy is transmitted toward the vicinity of the rear bearing 30. A first timer TIMER1 of the microprocessor 90 is then initialized and started by a block 114. Control then pauses at a block 116 until a first timer limit is reached. The first timer limit represents the minimum time before a return pulse is expected to be received by the element 40 or 70. Once the first timer limit is reached, a block 118 causes the microprocessor 90 to enter a capture mode of operation wherein the microprocessor 90 detects the output of the one-shot 106. If a pulse is received by the microprocessor 90, a capture register in the microprocessor is loaded with a non-zero value. The microprocessor remains in the capture mode until a block 120 determines that a second timer limit (representing the maximum time by which a return pulse should be received by the element 40 or 70) is reached.

Following the block 120 a block 122 checks to determine whether the capture register contains a non-zero value. If so, the counter COUNT is incremented by a block 124. Otherwise, the block 124 is skipped. Control then passes to a block 126, FIG. 6b, which increments the loop counter I. A block 128 checks to determine whether the current value of I is less than a certain value $I_L$, which, in the preferred embodiment, is equal to 100. If this is found to be the case, control returns to the block 112 of FIG. 6a. Otherwise, it has been determined that the element 40 or 70 has been pulsed the certain number of times represented by the value of $I_L$ and control passes to a block 130.

The block 130 determines whether the current value of COUNT is less than a threshold value THR. If this is not true, then it has been determined that the number of return pulses actually received by the element 40 or 70 as a result of applying $I_L$ trigger pulses thereto indicates that the bearing is not experiencing a dry bearing condition. Accordingly, a block 132 disables a dry bearing indicator controlled by the microprocessor 90 and deactuates a microprocessor timer TIMER2. Control then returns to the block 110 of FIG. 6a.

If the block 130 determines that the current value of COUNT is less than THR, then it has been determined that the number of received return pulses indicates a dry bearing condition. Accordingly, a block 134 checks to determine whether the timer TIMER2 is running. If not, the timer TIMER2 is initialized and started and the dry bearing indicator is actuated. If the timer TIMER2 is already running, then a dry bearing condition was detected during a previous pass through the programming, and hence the blocks 136 and 138 are skipped. Control then passes to a block 140 which determines whether a time limit for the timer TIMER2 has been reached. If not, control returns to the block 110 of FIG. 6a. Otherwise, it has been determined that the dry bearing condition has continuously existed for an unacceptably long period of time and hence a block 142 takes protective action in the form of energizing an alarm and/or shutting down the pump 10.

It should be noted that the single ultrasonic transducer 40 or 70 in either embodiment may be replaced by separate transmitting and receiving ultrasonic transducers, if desired. Also, the single microprocessor 90 may be replaced by different circuit(s) or by separate first and second microprocessors (or other separate circuits) which pulse the transducer 40 or 70 and serves return pulses, respectively.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the structure may be varied substantially without departing from the spirit of the invention, and the exclusive use of all modifications which come within the scope of the appended claims is reserved.

We claim:

1. Apparatus for detecting an operating condition of a bearing disposed in a bearing housing and subject to a dry bearing condition during which the bearing is not exposed to a bearing fluid, comprising:

an ultrasonic sensor directed toward the bearing housing and spaced therefrom;

an excitation circuit which provides excitation to the ultrasonic sensor to cause ultrasonic energy to be directed toward the bearing housing at a certain time across a space adapted to receive a bearing fluid; and a detection circuit including a timer which establishes a particular time period following the certain time during which a return pulse caused by reflection of the ultrasonic energy is expected to be received by the ultrasonic sensor when the bearing is not subjected to the dry bearing condition, the detection circuit further including means for determining whether reflected ultrasonic energy is not received by the ultrasonic sensor during the particular time period and means responsive to the determining means for developing an indication of a dry bearing condition.

2. The apparatus of claim 1, wherein the excitation circuit includes a microprocessor which causes the ultrasonic sensor to direct a pulse of ultrasonic energy toward the bearing housing.

3. The apparatus of claim 2, wherein the excitation circuit further includes a one-shot coupled to the microprocessor and a driver circuit coupled to the one-shot.

4. The apparatus of claim 1, wherein the detection circuit comprises a microprocessor.

5. The apparatus of claim 4, wherein the detection circuit further includes a comparator coupled to the ultrasonic sensor and a one-shot coupled between the comparator and the microprocessor.

6. The apparatus of claim 5, wherein the ultrasonic sensor is operated to direct a number of pulses of ultrasonic energy toward the bearing housing and wherein the microprocessor includes means for determining whether a certain number of return pulses of ultrasonic energy has been received by the ultrasonic sensor.

7. The apparatus of claim 1, wherein the ultrasonic sensor is radially spaced from the bearing.

8. The apparatus of claim 1, wherein the ultrasonic sensor is axially spaced from the bearing.

9. Apparatus for detecting an operating condition of a rotary bearing, comprising:

a piezoelectric transducer disposed remotely from the bearing and out of contact therewith and having a transducer face directed toward the vicinity of the bearing;

an excitation circuit for providing excitation to the piezoelectric transducer to cause ultrasonic energy to be directed across a space adapted to receive a bearing fluid toward the bearing vicinity; and a circuit for indicating that reflected ultrasonic energy is not being received at the piezoelectric transducer during a period of time after the ultrasonic energy is directed toward the bearing vicinity due to a dry bearing condition resulting from a lack of bearing fluid in the space.

10. The apparatus of claim 9, wherein the piezoelectric transducer is radially spaced from the bearing.

11. The apparatus of claim 9, wherein the piezoelectric transducer is axially spaced from the bearing.

12. The apparatus of claim 11, wherein the excitation circuit includes a microprocessor which causes the piezoelectric transducer to direct a pulse of ultrasonic energy toward the bearing.

13. The apparatus of claim 11, wherein the detection circuit includes a microprocessor which determines that a return pulse of ultrasonic energy has been received by the piezoelectric transducer.

14. The apparatus of claim 13, wherein the microprocessor includes a timer which establishes the time period during which a return pulse is expected to be received by the piezoelectric transducer.

15. Apparatus for detecting an operating condition of a rotary bearing, comprising:

means disposed remotely from the bearing and out of contact therewith for converting between electrical energy and acoustic energy;

means for exciting the converting means to cause a pulse of ultrasonic energy to be directed toward the bearing across a space adapted to receive a working fluid; and means coupled to the converting means for indicating whether reflected ultrasonic energy is not being received by the converting means during a period of time after the ultrasonic energy is directed toward the bearing due to a dry bearing condition resulting from a lack of working fluid in the space.

16. The apparatus of claim 15, wherein the converting means comprises a piezoelectric element.

17. The apparatus of claim 16, wherein the exciting means comprises a microprocessor.

18. The apparatus of claim 17, wherein the microprocessor includes a timer which establishes the period of time.

* * * * *